US012078812B2

(12) United States Patent
Hatfield et al.

(10) Patent No.: US 12,078,812 B2
(45) Date of Patent: Sep. 3, 2024

(54) HEAD-MOUNTABLE DEVICE FOR POSTURE DETECTION

(71) Applicant: Apple Inc., Cupertino, CA (US)

(72) Inventors: Dustin A. Hatfield, Campbell, CA (US); Kam Mui C. Siu, Santa Clara, CA (US); Angela M. Avera, San Francisco, CA (US)

(73) Assignee: Apple Inc., Cupertino, CA (US)

(*) Notice: Subject to any disclaimer, the term of this patent is extended or adjusted under 35 U.S.C. 154(b) by 0 days.

(21) Appl. No.: 18/125,594

(22) Filed: Mar. 23, 2023

(65) Prior Publication Data

US 2023/0229010 A1    Jul. 20, 2023

Related U.S. Application Data

(63) Continuation of application No. PCT/US2021/047671, filed on Aug. 26, 2021.
(Continued)

(51) Int. Cl.
*G02B 27/01*    (2006.01)

(52) U.S. Cl.
CPC ..... *G02B 27/0179* (2013.01); *G02B 27/0101* (2013.01); *G02B 27/017* (2013.01);
(Continued)

(58) Field of Classification Search
CPC ............ G02B 27/0179; G02B 27/0101; G02B 27/017; G02B 2027/0138;
(Continued)

(56) References Cited

U.S. PATENT DOCUMENTS

| 2010/0045469 | A1* | 2/2010 | Reijndorp | ............... G06F 3/023 |
| | | | | 340/573.7 |
| 2014/0028458 | A1* | 1/2014 | Shin | ..................... G06V 40/103 |
| | | | | 340/573.7 |

(Continued)

FOREIGN PATENT DOCUMENTS

| CN | 108389372 | A | * | 8/2018 | ............. G06F 3/012 |
| JP | 2004236241 | A | * | 8/2004 | |
| JP | 4497305 | B2 | * | 7/2010 | ............. A61B 3/113 |

OTHER PUBLICATIONS

"A Method for Adjusting the User's Posture while using a Digital Device by Adjusting the Screen Content in Real-Time"; ip.com; Sep. 7, 2020; 6 pages. (Year: 2020).*

(Continued)

*Primary Examiner* — Temesghen Ghebretinsae
*Assistant Examiner* — Karin Kiyabu
(74) *Attorney, Agent, or Firm* — BAKERHOSTETLER

(57) ABSTRACT

While head-mountable devices can provide immersive experiences, a user wearing a head-mountable device can also benefit from activities that include body motion and promote the user's health. Because such activities may not be intrinsically necessary to the operation of head-mountable devices, it can be beneficial to provide additional or modified operations that allow a user to continue operation of a head-mountable device while performing the desired body motions. The head-mountable device can detect movement and/or stasis of the user and determine whether motion would be recommended. Upon determining that motion, an additional motion, or a different motion would be beneficial, the head-mountable device can provide an output to the user that promote such motions. The output can include a notification to the user and/or a modification of the user interface that encourages the user to move in a particular way.

19 Claims, 6 Drawing Sheets

Related U.S. Application Data

(60) Provisional application No. 63/082,976, filed on Sep. 24, 2020.

(52) U.S. Cl.
CPC ............... *G02B 2027/0138* (2013.01); *G02B 2027/014* (2013.01); *G02B 2027/0187* (2013.01)

(58) Field of Classification Search
CPC ...... G02B 2027/014; G02B 2027/0187; A61B 5/1116; G06F 3/0346; G06F 3/011
See application file for complete search history.

(56) References Cited

U.S. PATENT DOCUMENTS

| | | | | |
|---|---|---|---|---|
| 2017/0139472 A1* | 5/2017 | Basile, Jr. | ............ | G06F 3/0346 |
| 2017/0358241 A1* | 12/2017 | Wexler | ................... | G06V 40/10 |
| 2019/0172261 A1* | 6/2019 | Alt | .......................... | G06T 19/20 |
| 2020/0201048 A1 | 6/2020 | Nakata et al. | | |
| 2020/0261767 A1 | 8/2020 | Fung | | |
| 2023/0419794 A1* | 12/2023 | Aoki | ....................... | G08B 6/00 |

OTHER PUBLICATIONS

Invitation to Pay Additional Fees from PCT/US2021/047671, dated Dec. 7, 2021, 11 pages.
International Preliminary Report on Patentability from PCT/US2021/047674, dated Apr. 6, 2023, 12 pages.

\* cited by examiner

HEAD-MOUNTABLE DEVICE FOR POSTURE DETECTION

CROSS-REFERENCE TO RELATED APPLICATIONS

This application is a continuation of International Application No. PCT/US2021/0047671, entitled "HEAD-MOUNTABLE DEVICE FOR POSTURE DETECTION," filed Aug. 26, 2021, which claims the benefit of U.S. Provisional Application No. 63/082,976, entitled "HEAD-MOUNTABLE DEVICE FOR POSTURE DETECTION," filed Sep. 24, 2020, the entirety of which is incorporated herein by reference.

TECHNICAL FIELD

The present description relates generally to head-mountable devices, and, more particularly, to posture detection and related outputs with head-mountable devices.

BACKGROUND

A head-mountable device can be worn by a user to display visual information within the field of view of the user. The head-mountable device can be used as a virtual reality (VR) system, an augmented reality (AR) system, and/or a mixed reality (MR) system. A user may observe outputs provided by the head-mountable device, such as visual information provided on a display. The display can optionally allow a user to observe an environment outside of the head-mountable device. Other outputs provided by the head-mountable device can include speaker output and/or haptic feedback. A user may further interact with the head-mountable device by providing inputs for processing by one or more components of the head-mountable device. For example, the user can provide tactile inputs, voice commands, and other inputs while the device is mounted to the user's head.

BRIEF DESCRIPTION OF THE DRAWINGS

Certain features of the subject technology are set forth in the appended claims. However, for purpose of explanation, several embodiments of the subject technology are set forth in the following figures.

DETAILED DESCRIPTION

Figure 1:
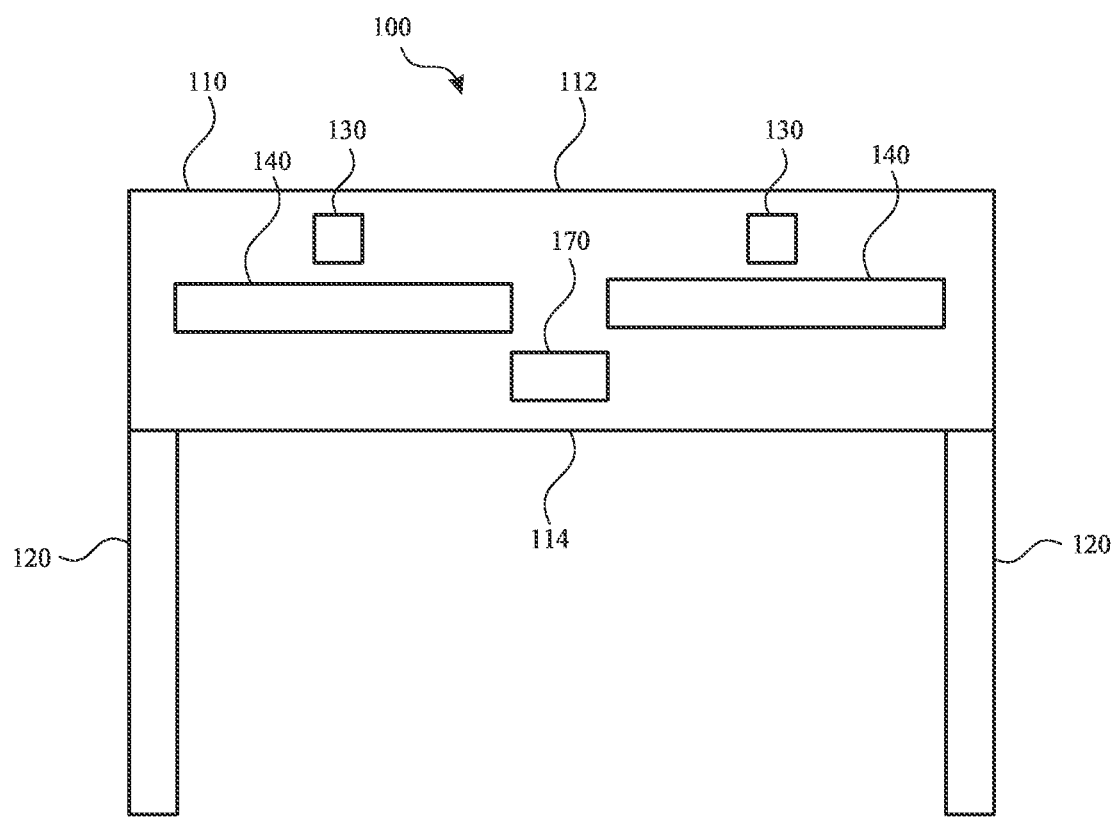
FIG. 1 illustrates a top view of a head-mountable device, according to some embodiments of the present disclosure.

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, it will be clear and apparent to those skilled in the art that the subject technology is not limited to the specific details set forth herein and may be practiced without these specific details. In some instances, well-known structures and components are shown in block diagram form in order to avoid obscuring the concepts of the subject technology.

Head-mountable devices, such as head-mountable displays, headsets, visors, smartglasses, head-up display, etc., can perform a range of functions that are managed by the components (e.g., sensors, circuitry, and other hardware) included with the wearable device. The head-mountable device can provide a user experience that is immersive or otherwise natural so the user can easily focus on enjoying the experience without being distracted by the mechanisms of the head-mountable device.

A person can benefit from certain motions that promote the user's health. Regardless of whether such motions include rigorous cardiovascular activity, a person can benefit from small motions that break up long periods of maintaining a stationary posture or pose. Such motions, performed at least occasionally, periodically, and/or sporadically, can promote the health of the user, particularly in the portions of the body where such motions are performed. Such health benefits can include greater comfort, posture, flexibility, mobility, stability, balance, coordination, athletic performance, and range of motion. Such health benefits can be realized within a short period of time (e.g., within a session of wearing a head-mountable device) and/or across a long period of time (e.g., across multiple sessions of wearing a head-mountable device).

Head-mountable devices can be worn and operated by a user for extended periods of time, in which certain movements by the user are not intrinsically necessary for the operations and/or experience provided by the head-mountable device. For example, some operations of a head-mountable device can optionally be performed while the user is partially or completely stationary. If the user remains stationary for extended periods of time, the user may not enjoy the benefits of body motion, as described herein. At the same time, it can be disruptive to the user's experience with the head-mountable device to require that the user remove the head-mountable device and perform certain body motions.

While head-mountable devices can provide immersive experiences, a user wearing a head-mountable device can also benefit from activities that include body motion and promote the user's health. Because such activities may not be intrinsically necessary to the operation of head-mountable devices, it can be beneficial to provide additional or modified operations that allow a user to continue operation of a head-mountable device while performing the desired body motions. The head-mountable device can detect movement and/or stasis of the user and determine whether motion would be recommended. Upon determining that motion, an additional motion, or a different motion would be beneficial, the head-mountable device can provide an output to the user that promote such motions. The output can include a notification to the user and/or a modification of the user interface that encourages the user to move in a particular way.

These and other embodiments are discussed below with reference to FIGS. 1-9. However, those skilled in the art will readily appreciate that the detailed description given herein with respect to these Figures is for explanatory purposes only and should not be construed as limiting.

According to some embodiments, for example as shown in FIG. 1, a head-mountable device 100 includes a frame 110 that is worn on a head of a user. The frame 110 can be positioned in front of the eyes of a user to provide information within a field of view of the user. The frame 110 can provide nose pads or another feature to rest on a user's nose. The frame 110 can be supported on a user's head with the securement element 120. The securement element 120 can wrap or extend along opposing sides of a user's head. The securement element 120 can include earpieces for wrapping around or otherwise engaging or resting on a user's ears. It will be appreciated that other configurations can be applied for securing the head-mountable device 100 to a user's head. For example, one or more bands, straps, belts, caps, hats, or other components can be used in addition to or in place of the illustrated components of the head-mountable device 100. By further example, the securement element 120 can include multiple components to engage a user's head.

The frame 110 can provide structure around a peripheral region thereof to support any internal components of the frame 110 in their assembled position. For example, the frame 110 can enclose and support various internal components (including for example integrated circuit chips, processors, memory devices and other circuitry) to provide computing and functional operations for the head-mountable device 100, as discussed further herein. Any number of components can be included within and/or on the frame 110 and/or the securement element 120.

The frame 110 can include and/or support one or more cameras 130. The cameras 130 can be positioned on or near an outer side 112 of the frame 110 to capture images of views external to the head-mountable device 100. As used herein, an outer side 112 of a portion of a head-mountable device is a side that faces away from the user and/or towards an external environment. The captured images can be used for display to the user or stored for any other purpose.

The head-mountable device can be provided with one or more displays 140 that provide visual output for viewing by a user wearing the head-mountable device. As shown in FIG. 1, one or more optical modules containing displays 140 can be positioned on an inner side 114 of the frame 110. As used herein, an inner side of a portion of a head-mountable device is a side that faces toward the user and/or away from the external environment. For example, a pair of optical modules can be provided, where each optical module is movably positioned to be within the field of view of each of a user's two eyes. Each optical module can be adjusted to align with a corresponding eye of the user. Movement of each of the optical modules can match movement of a corresponding camera 130. Accordingly, the optical module is able to accurately reproduce, simulate, or augment a view based on a view captured by the camera 130 with an alignment that corresponds to the view that the user would have naturally without the head-mountable device 100.

A display 140 can transmit light from a physical environment (e.g., as captured by a camera) for viewing by the user. Such a display can include optical properties, such as lenses for vision correction based on incoming light from the physical environment. Additionally or alternatively, a display 140 can provide information as a display within a field of view of the user. Such information can be provided to the exclusion of a view of a physical environment or in addition to (e.g., overlaid with) a physical environment.

A physical environment refers to a physical world that people can sense and/or interact with without aid of electronic systems. Physical environments, such as a physical park, include physical articles, such as physical trees, physical buildings, and physical people. People can directly sense and/or interact with the physical environment, such as through sight, touch, hearing, taste, and smell.

In contrast, a computer-generated reality (CGR) environment refers to a wholly or partially simulated environment that people sense and/or interact with via an electronic system. In CGR, a subset of a person's physical motions, or representations thereof, are tracked, and, in response, one or more characteristics of one or more virtual objects simulated in the CGR environment are adjusted in a manner that comports with at least one law of physics. For example, a CGR system may detect a person's head turning and, in response, adjust graphical content and an acoustic field presented to the person in a manner similar to how such views and sounds would change in a physical environment. In some situations, (e.g., for accessibility reasons), adjustments to characteristic(s) of virtual object(s) in a CGR environment may be made in response to representations of physical motions (e.g., vocal commands).

A person may sense and/or interact with a CGR object using any one of their senses, including sight, sound, touch, taste, and smell. For example, a person may sense and/or interact with audio objects that create 3D or spatial audio environment that provides the perception of point audio sources in 3D space. In another example, audio objects may enable audio transparency, which selectively incorporates ambient sounds from the physical environment with or without computer-generated audio. In some CGR environments, a person may sense and/or interact only with audio objects.

Examples of CGR include virtual reality and mixed reality.

A virtual reality (VR) environment refers to a simulated environment that is designed to be based entirely on computer-generated sensory inputs for one or more senses. A VR environment comprises a plurality of virtual objects with which a person may sense and/or interact. For example, computer-generated imagery of trees, buildings, and avatars representing people are examples of virtual objects. A person may sense and/or interact with virtual objects in the VR environment through a simulation of the person's presence within the computer-generated environment, and/or through a simulation of a subset of the person's physical movements within the computer-generated environment.

In contrast to a VR environment, which is designed to be based entirely on computer-generated sensory inputs, a mixed reality (MR) environment refers to a simulated environment that is designed to incorporate sensory inputs from the physical environment, or a representation thereof, in addition to including computer-generated sensory inputs (e.g., virtual objects). On a virtuality continuum, a mixed reality environment is anywhere between, but not including, a wholly physical environment at one end and virtual reality environment at the other end.

In some MR environments, computer-generated sensory inputs may respond to changes in sensory inputs from the physical environment. Also, some electronic systems for presenting an MR environment may track location and/or orientation with respect to the physical environment to enable virtual objects to interact with real objects (that is, physical articles from the physical environment or representations thereof). For example, a system may account for movements so that a virtual tree appears stationery with respect to the physical ground.

Examples of mixed realities include augmented reality and augmented virtuality.

An augmented reality (AR) environment refers to a simulated environment in which one or more virtual objects are superimposed over a physical environment, or a representation thereof. For example, an electronic system for presenting an AR environment may have a transparent or translucent display through which a person may directly view the physical environment. The system may be configured to present virtual objects on the transparent or translucent display, so that a person, using the system, perceives the virtual objects superimposed over the physical environment. Alternatively, a system may have an opaque display and one or more imaging sensors that capture images or video of the physical environment, which are representations of the physical environment. The system composites the images or video with virtual objects, and presents the composition on the opaque display. A person, using the system, indirectly views the physical environment by way of the images or video of the physical environment, and perceives the virtual objects superimposed over the physical environment. As used herein, a video of the physical environment shown on an opaque display is called "pass-through video," meaning a system uses one or more image sensor(s) to capture images of the physical environment, and uses those images in presenting the AR environment on the opaque display. Further alternatively, a system may have a projection system that projects virtual objects into the physical environment, for example, as a hologram or on a physical surface, so that a person, using the system, perceives the virtual objects superimposed over the physical environment.

An augmented reality environment also refers to a simulated environment in which a representation of a physical environment is transformed by computer-generated sensory information. For example, in providing pass-through video, a system may transform one or more sensor images to impose a select perspective (e.g., viewpoint) different than the perspective captured by the imaging sensors. As another example, a representation of a physical environment may be transformed by graphically modifying (e.g., enlarging) portions thereof, such that the modified portion may be representative but not photorealistic versions of the originally captured images. As a further example, a representation of a physical environment may be transformed by graphically eliminating or obfuscating portions thereof An augmented virtuality (AV) environment refers to a simulated environment in which a virtual or computer generated environment incorporates one or more sensory inputs from the physical environment. The sensory inputs may be representations of one or more characteristics of the physical environment. For example, an AV park may have virtual trees and virtual buildings, but people with faces photorealistically reproduced from images taken of physical people. As another example, a virtual object may adopt a shape or color of a physical article imaged by one or more imaging sensors. As a further example, a virtual object may adopt shadows consistent with the position of the sun in the physical environment.

There are many different types of electronic systems that enable a person to sense and/or interact with various CGR environments. Examples include head-mountable systems, projection-based systems, heads-up displays (HUDs), vehicle windshields having integrated display capability, windows having integrated display capability, displays formed as lenses designed to be placed on a person's eyes (e.g., similar to contact lenses), headphones/earphones, speaker arrays, input systems (e.g., wearable or handheld processors with or without haptic feedback), smartphones, tablets, and desktop/laptop computers. A head-mountable system may have one or more speaker(s) and an integrated opaque display. Alternatively, a head-mountable system may be configured to accept an external opaque display (e.g., a smartphone). The head-mountable system may incorporate one or more imaging sensors to capture images or video of the physical environment, and/or one or more microphones to capture audio of the physical environment. Rather than an opaque display, a head-mountable system may have a transparent or translucent display. The transparent or translucent display may have a medium through which light representative of images is directed to a person's eyes. The display may utilize digital light projection, OLEDs, LEDs, uLEDs, liquid crystal on silicon, laser scanning light source, or any combination of these technologies. The medium may be an optical waveguide, a hologram medium, an optical combiner, an optical reflector, or any combination thereof. In one embodiment, the transparent or translucent display may be configured to become opaque selectively. Projection-based systems may employ retinal projection technology that projects graphical images onto a person's retina. Projection systems also may be configured to project virtual objects into the physical environment, for example, as a hologram or on a physical surface.

As further shown in FIG. 1, the head-mountable device 100 can include a posture detection system 170. The posture detection system 170 can include one or more sensors that are operable to detect a position and/or orientation of the head-mountable device 100 and/or one or more body portions of the user wearing the head-mountable device 100. The detection of a position and/or orientation can be relative to a fixed frame of reference (e.g., gravitational), another device, and/or a body portion of the user. Detections by the posture detection system 170 can be used to prompt movement of the user to promote the user's health, as described further herein.

In one or more implementations, the head-mountable device 100 can detect the posture and/or stasis by one or more onboard sensors that form the posture detection system 170. For example, the posture detection system 170 can include an initial measurement unit ("IMU") that provides information regarding a characteristic of the head-mounted device, such as inertial angles thereof. For example, the IMU can include a six-degrees of freedom IMU that calculates the head-mounted device's position, velocity, and/or acceleration based on six degrees of freedom (x, y, z, $\theta_x$, $\theta_y$, and $\theta_z$). The IMU can include one or more of an accelerometer, a gyroscope, and/or a magnetometer. Additionally or alternatively, the head-mounted device can detect motion characteristics of the head-mounted device with one or more other motion sensors, such as an accelerometer, a gyroscope, a global positioning sensor, a tilt sensor, and so on for detecting movement and acceleration of the head-mounted device.

The posture detection system 170 can include one or more other sensors, such as image sensors (e.g., cameras), infrared sensors, depth sensors, thermal (e.g., infrared) sensors, and the like. The posture detection system 170 can include or operate in concert with sensors of one or more external devices that are operably and/or communicatively connected to the head-mountable device 100. For example, the posture detection system 170 can include or be connected to one or more wired or wireless communication interfaces, such as one or more universal serial bus (USB) interfaces, near-field communication (NFC) radios, wireless local area network (WLAN) radios, Bluetooth radios, Zigbee radios, cellular radios, and/or other wireless radios. Such external devices can detect a characteristic of the head-mountable device 100 and/or the user and communicate the results of such detections to the head-mountable device 100. Additionally or alternatively, the head-mountable device 100 can detect a characteristic of one or more external devices, which can provide a frame of reference for the head-mountable device 100.

Figure 2:
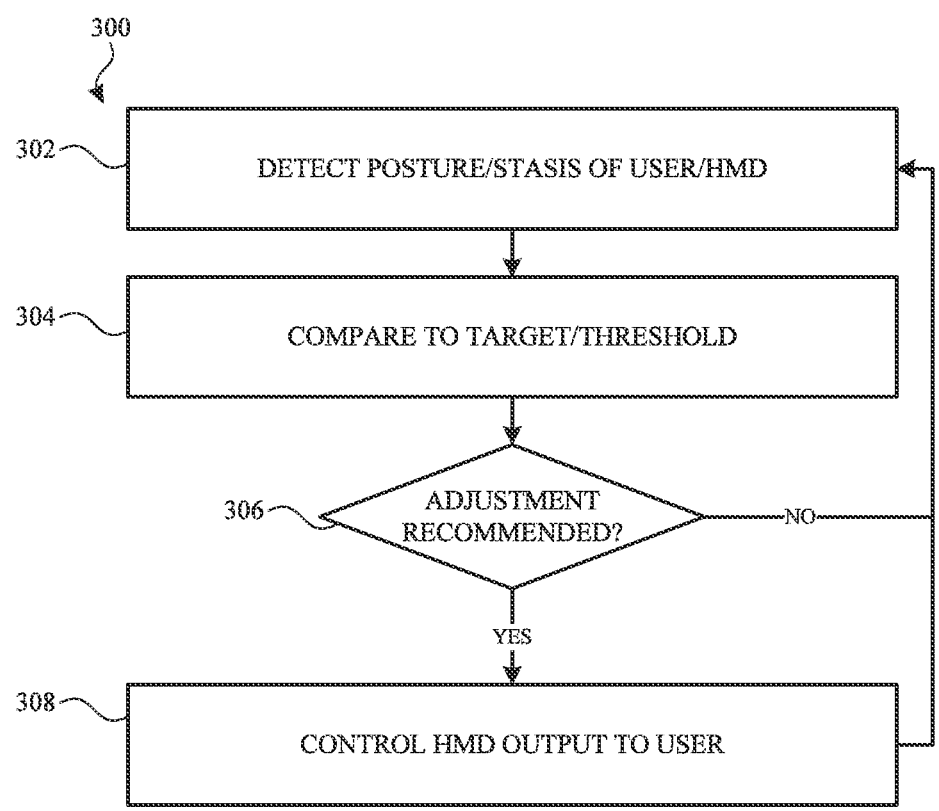
FIG. 2 illustrates a flow diagram of an example process for posture detection and related output, according to some embodiments of the present disclosure.

FIG. 2 illustrates a flow diagram of an example process 300 for posture detection and related output in accordance with one or more implementations. For explanatory purposes, the process 300 is primarily described herein with reference to the head-mountable device 100 and of FIG. 1. However, the process 300 is not limited to the head-mountable device 100 of FIG. 1, and one or more blocks (or operations) of the process 300 may be performed by one or more other components or chips of the head-mountable device 100 and/or an external device. Such external devices can other devices worn by the user and/or devices that are apart from the user. The head-mountable device 100 also is presented as an exemplary device and the operations described herein may be performed by any suitable device. Further, for explanatory purposes, the blocks of the process 300 are described herein as occurring in serial, or linearly. However, multiple blocks of the process 300 may occur in parallel. In addition, the blocks of the process 300 need not be performed in the order shown and/or one or more blocks of the process 300 need not be performed and/or can be replaced by other operations.

The process 300 can begin when the head-mountable device and/or an external device detects a posture and/or stasis of the user and/or the head-mountable device (302). In one or more implementations, the head-mountable device can detect the posture and/or stasis by one or more onboard sensors that form a posture detection system. In one or more implementations, the posture detection system can include or operate in concert with sensors of one or more external devices that are operably and/or communicatively connected to the head-mountable device. As such, the detection of posture and/or stasis can be based on the operations of the head-mountable device and/or an external device.

As used herein, a "posture" of a user is a physical position and/or orientation of one body portion of the user with respect to another body portion of the user. It will be understood that such body portions can be can connected to each other by joints and that such relative positions and orientations can be changed by movement of the user. As an example, the position and/or orientation of the head relative to the torso of the user can be defined by the connection along the neck. It will be understood that posture can include the relative position of any two body portions of the user. For example, posture can be defined by the position and/or orientation of one or more arms relative to the torso (i.e., as joined by the shoulder), one or more hands relative to the arms (i.e., as joined by the wrist), one or more fingers relative to the hands, and the like. By further example, posture can be defined by the position and/or orientation of one or more legs relative to the torso (i.e., as joined by the hip), one or more feet relative to the legs (i.e., as joined by the ankle), one or more toes relative to the legs, and the like.

As used herein, "stasis" is a condition in which movement is absent or limited in at least one way across a duration of time. A user can present stasis in one or more body portions by not moving or by limiting movement for a duration of time. It will be understood that stasis can occur in one body portion while other body portions are moving.

Based on the detected posture and/or stasis of the user and/or the head-mountable device, the detected conditions can be compared to certain criteria to determine whether adjustments are recommended (304). For example, a current posture can be compared to a target posture to determine whether the current posture conforms to the target posture or whether an adjustment is recommended to achieve the target posture. By further example, the head-mountable device can analyze the detected posture and/or stasis to determine whether a particular posture has been maintained for a duration of time that exceeds a threshold. While the duration of time can provide one threshold, the degree of movement can provide an additional or alternative threshold. For example, small movements performed within the duration of time can be such that they are inadequate to provide to the user the benefits of certain motions. By further example, one or more characteristics of movements (e.g., direction, speed, acceleration, duration) can be compared to corresponding thresholds. One or more of such detected conditions can be compared to corresponding thresholds to determine whether adjustments are recommended. It will be understood that multiple factors can be considered to determine whether adjustments are recommended Based on the comparison of detected conditions to corresponding target tender thresholds, the head-mountable device can determine whether an adjustment is recommended for the user (306). Such an adjustment can be considered as being recommended when the user has exceeded a threshold and/or deviated from a target. If no such adjustment is recommended or necessary, then the process can terminate and/or begin to detect anew.

If the head-mountable device determines that an adjustment is recommended or necessary, head-mountable device can control an output to the user (308). The output can be one that promotes or encourages the user to take actions that correspond to the recommended adjustment. The output can comprise a visual element, a sound, haptic feedback, and the like.

For example, the head-mountable device can provide a notification, alarm, signal, reminder, and/or instruction to the user indicating that the user should make the recommended adjustment and/or how such could be achieved. Such an output can be over, such that the user is aware and the head-mountable device relies on the user's compliance to make the recommended adjustment.

It will be recognized that other types of outputs are contemplated. For example, the head-mountable device can provide an output that encourages the user without disrupting the user's experience with the head-mountable device. Such outputs can include modifications to other outputs already provided by the head-mountable device, as described further herein.

It will be further recognized that other characteristics of a user can be monitored and evaluated to determine whether an adjustment is recommended. For example, the user's vision and/or gaze can be monitored to alleviate eye fatigue.

Where a user has focused on near objects for a duration or proportion of time, the head-mountable device can prompt the user to observe and/or focus on a distant object for a time. It will be understood that such objects can be physical and/or virtual. It will be further understood that the distance to an object can be based on a representation that causes an object to appear at a particular distance via the optical properties of the head-mountable device.

Referring now to FIGS. 3-8, a head-mountable device can be operated to provide outputs, such as visual elements on a user interface of the display, to promote posture adjustments by the user.

Figure 3:
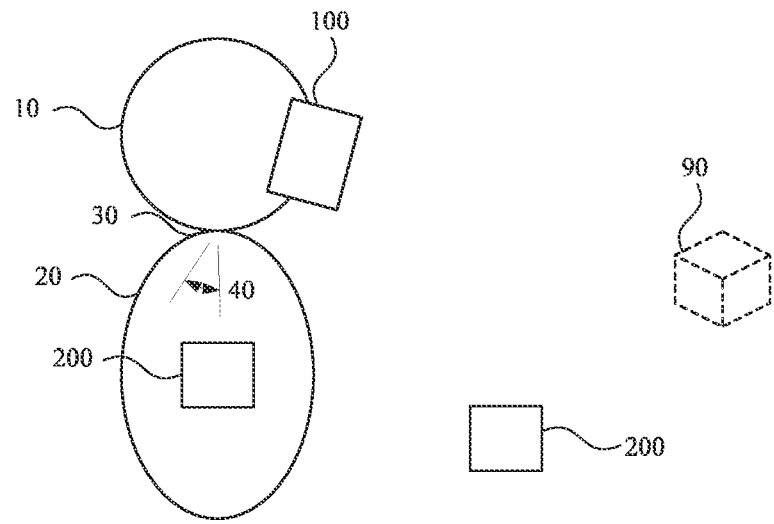
FIG. 3 illustrates a view of a head-mountable device worn by a user, according to some embodiments of the present disclosure.

As shown in FIG. 3, the head-mountable device 100 can be worn on a head 10 of the user. The head 10 of the user can form an angle 40 with respect to the torso 20 or another body portion of the user. For example, the user can pivot the head 10 at the neck 30 to adjust the angle 40. It will be understood that the body portions for comparison can be any two or more body portions.

The head-mountable device 100 can be operated independently and/or in concert with one or more external devices 200. For example, an external device 200 can be worn on the torso 20 or other body portion of the user. By further example, an external device 200 can be one that is not worn by the user, but is otherwise positioned in a vicinity of the user and/or the head-mountable device 100. The head-mountable device 100 and/or the one or more external devices 200 can monitor their own conditions and/or conditions of each other and/or the user.

The head-mountable device 100 can provide a view of a physical or virtual object as a visual element 90. It will be understood that the view can correspond to an image captured by a camera of the head-mountable device 100. Additionally or alternatively, the view can include virtual objects that may or may not correspond to physical objects.

Figure 4:
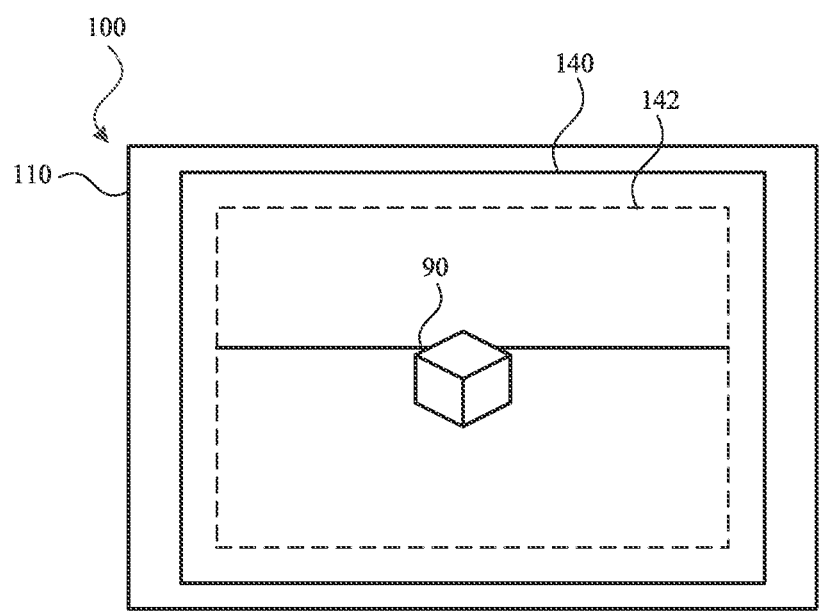
FIG. 4 illustrates the head-mountable device of FIG. 3 displaying an example user interface, according to some embodiments of the present disclosure.

Referring now to FIG. 4, a head-mountable device can provide a user interface that provides information based on posture detections. FIG. 4 illustrates a rear view of a head-mountable device operable by a user, the head-mountable device providing a user interface, according to some embodiments of the present disclosure. The display 140 can provide a user interface 142. Not all of the depicted graphical elements may be used in all implementations, however, and one or more implementations may include additional or different graphical elements than those shown in the figure. Variations in the arrangement and type of the graphical elements may be made without departing from the spirit or scope of the claims as set forth herein. Additional components, different components, or fewer components may be provided.

As shown in FIG. 4, the user interface 142 can include a depiction of a visual element 90. The object can correspond to a physical object captured by a camera of the head-mountable device 100 or another object, such as a virtual object, menu, text, image, and the like. It will be understood that the head-mountable device 100 can be operated in a manner that allows the user to adjust the view by moving and/or rotating the head-mountable device 100. As such, the user's view can be maintained at least somewhat during periods of stasis and/or sustained posture.

Figure 5:
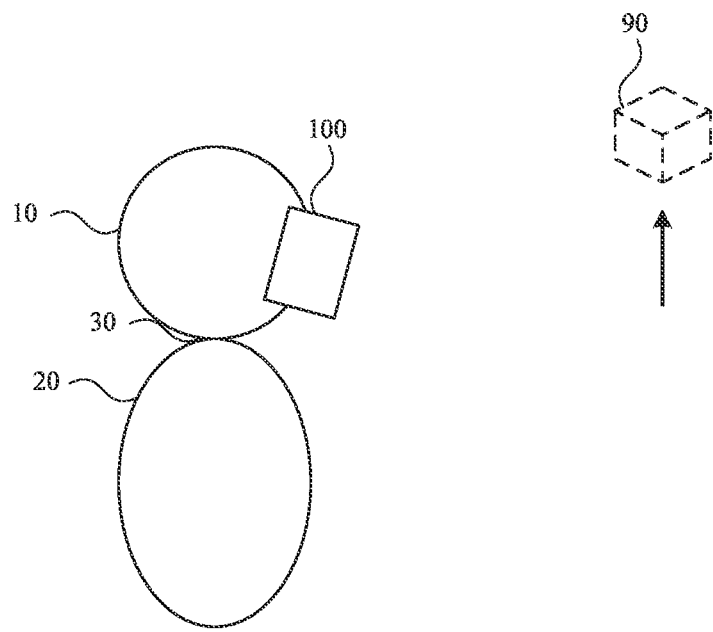
FIG. 5 illustrates a view of a head-mountable device worn by a user, according to some embodiments of the present disclosure.
Figure 6:
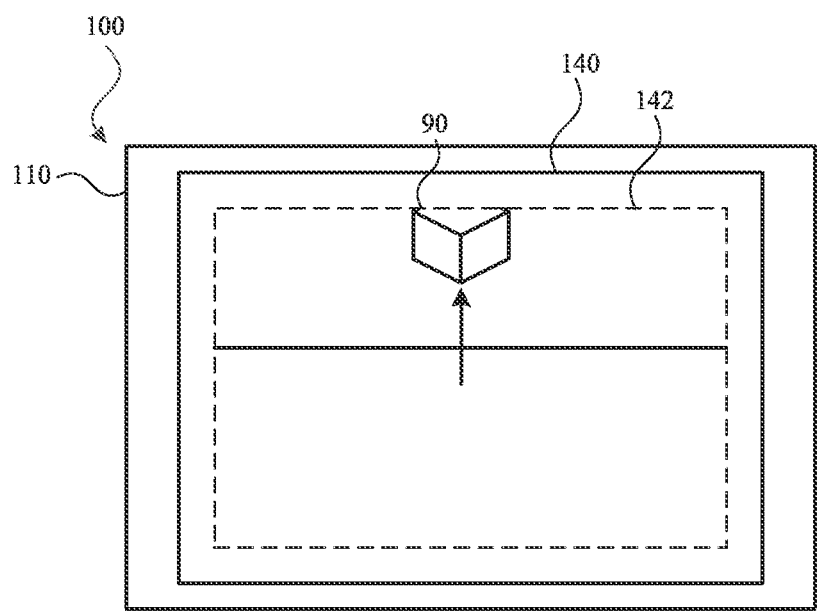
FIG. 6 illustrates the head-mountable device of FIG. 5 displaying an example user interface, according to some embodiments of the present disclosure.

Referring now to FIGS. 5 and 6, an output provided by the head-mountable device 100 can include movement and/or presentation of a visual element 90. For example, the user interface can be altered somewhat in response to a detection relating to stasis and/or a sustained posture of the user and/or the head-mountable device 100. Upon such detection and/or determination that adjustment is recommended, a visual element can be provided to encourage the user to make the recommended adjustments and/or achieve a target posture.

As shown in FIGS. 5 and 6, the visual element 90 can be moved to and/or provided at a side of the user interface 142 that corresponds to a direction of the recommended adjustment by the user. For example, where the recommended adjustment includes rotating the head up word with respect to a torso of the user, the visual element 90 can be moved and/or provided had an upper side of the user interface to encourage the user to move the head to bring and maintain the visual element 90 within a central region of the user interface 142. By further example, at least a portion of the visual element 90 can be moved outside of the view user interface 142. Such an action can be provided as an animation to notify the user of the shift so that the user can move the head in a direction that maintains the visual element 90 within a field of view of the user. In some embodiments, the adjustment of the visual element 90 can be made in stages. For example, the visual element 90 can be moved to a side of the user interface 142 in a first stage. In a later stage, for example if the user does not move to the target posture, the visual element 90 can be moved out of the user interface 142, so that the user is required to move the head 10 to return the visual element 90 to be within the user interface 142.

Figure 7:
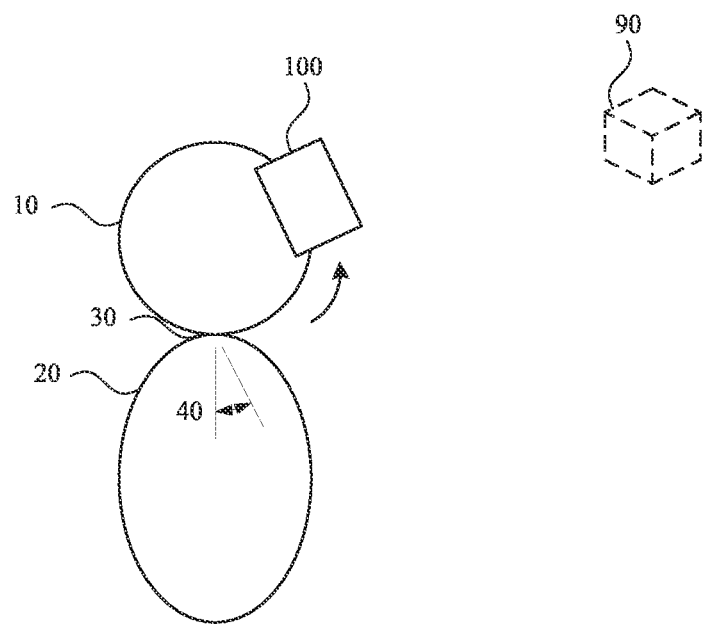
FIG. 7 illustrates a view of a head-mountable device worn by a user, according to some embodiments of the present disclosure.
Figure 8:
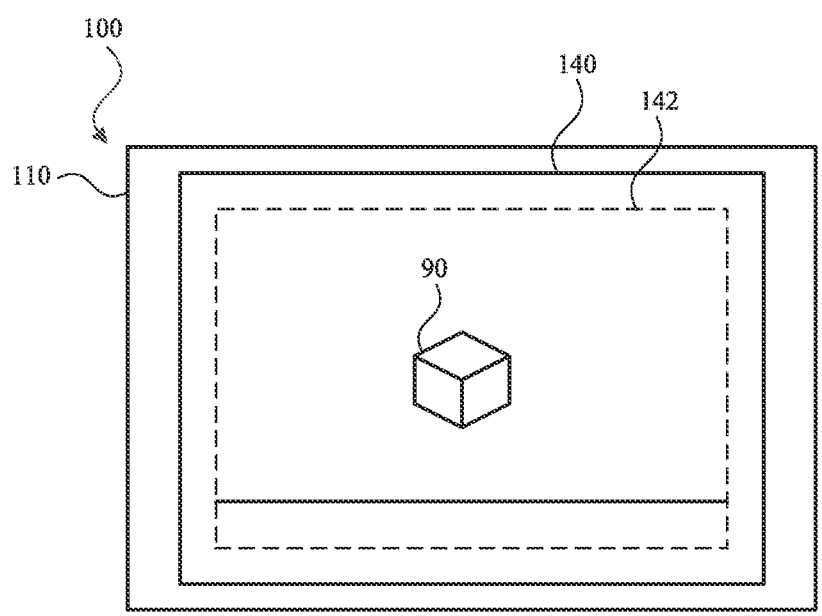
FIG. 8 illustrates the head-mountable device of FIG. 7 displaying an example user interface, according to some embodiments of the present disclosure.

Referring now to FIGS. 7 and 8, the user can move the head or other body portion. As the user moves the head 10 and the head-mountable device 100, the visual element 90 is correspondingly moved within the user interface 142. Such actions can serve as a reward for moving to the target posture. In such a posture, the head 10 and the torso 20 or other body portion can form a second angle 40 that is different than the prior angle 40.

Other types of output can be provided to prompt a user to make adjustments. For example, the outputs can include instructions to move in a particular way. Additionally or alternatively, content can be remove or modified until the user makes the recommended adjustment. For example, visual elements can be presented as blurry, blocked, occluded, dim, and/or transparent until the user makes the recommended adjustment. Additionally or alternatively, content can be added or modified until the user makes the recommended adjustment. For example, visual elements can be presented as highlighted, opaque, and/or brighter until the user makes the recommended adjustment. Outputs include visual elements, sound, haptic feedback, and the like.

It will be understood that adjustments of visual elements as described herein can be repeated as needed to achieve different target postures after successive durations of time. As such, the outputs can be dynamically updated based on multiple detections and determinations as described herein.

It will be further understood that the objective of adjusting a current posture and/or achieving a target posture can include multiple stages. For example, the user can be prompted to perform a sequence of movements to achieve each of different target postures. Such a sequence can promote flexibility and mobility in multiple dimensions.

It will be further understood that such measures can be temporary. For example, the user can be prompted to take certain actions. Thereafter, the user can resume operation according to a prior mode until adjustments are again determined to be recommended.

It will be further understood that other adjustments to visual elements or other outputs can be provided to prompt the user to make recommended adjustments to posture. For example, a visual element or certain functionality of the head-mountable device 100 can be revoked or omitted until the user performs a recommended adjustment to posture and/or until the user achieves a target posture. Upon such user action, the visual element or other functionality of the head-mountable device 100 can be restored.

For example, the user can be blocked from access to certain functions (e.g., apps, programs, content, experiences, commands, outputs, and the like) until certain actions are performed by the user according to the recommended adjustment. Such actions can include moving in a way that adjusts the user's posture. Additionally or alternatively, such actions can include movement by the user to a target location. Additionally or alternatively, such actions can include looking at a particular object (e.g., at a set distance to relief eye fatigue) and/or in a particular direction.

Where the user is recommended to make particular adjustments, the outputs of the head-mountable device 100 can encourage such adjustments by providing indicators (e.g., visual, audio, and the like) to draw the user's attention. Accordingly, such adjustments can be incorporated into the regular operations of the head-mountable device 100 so that the adjustments made by the user feel like a natural part of the experience with the head-mountable device 100.

Recommended adjustments applied by the head-mountable device 100 can include recommendations that the user assume a particular posture for a short duration of time and/or a long duration of time. For example, the head-mountable device 100 can prompt the user to make movements as a temporary measure to ameliorate detected conditions, including stasis. By further example, the head-mountable device 100 can prompt the user to assume a substantially persistent posture, such as sitting, standing, reclining, and the like. Such a recommendation can be based on detected conditions, operations of the head-mountable device 100, and the like. For example, the head-mountable device 100 may recommend different postures at least temporarily for different activities, such as gaming, watching video content, and/or composing messages.

Other recommendations can include adjusting a fit and/or configuration of the head-mountable device 100. For example, the head-mountable device 100 can recommend that the user adjust the fit, position, orientation, and/or tightness of the head-mountable device 100 on the head of the user. By further example, the head-mountable device 100 can recommend that the user adjust the head-mountable device 100 to provide a different effect on the user. Such adjustments can include exchanging modules, removing modules, and/or adding modules, such as a counter-balance to adjust the weight distribution of the head-mountable device 100.

Figure 9:
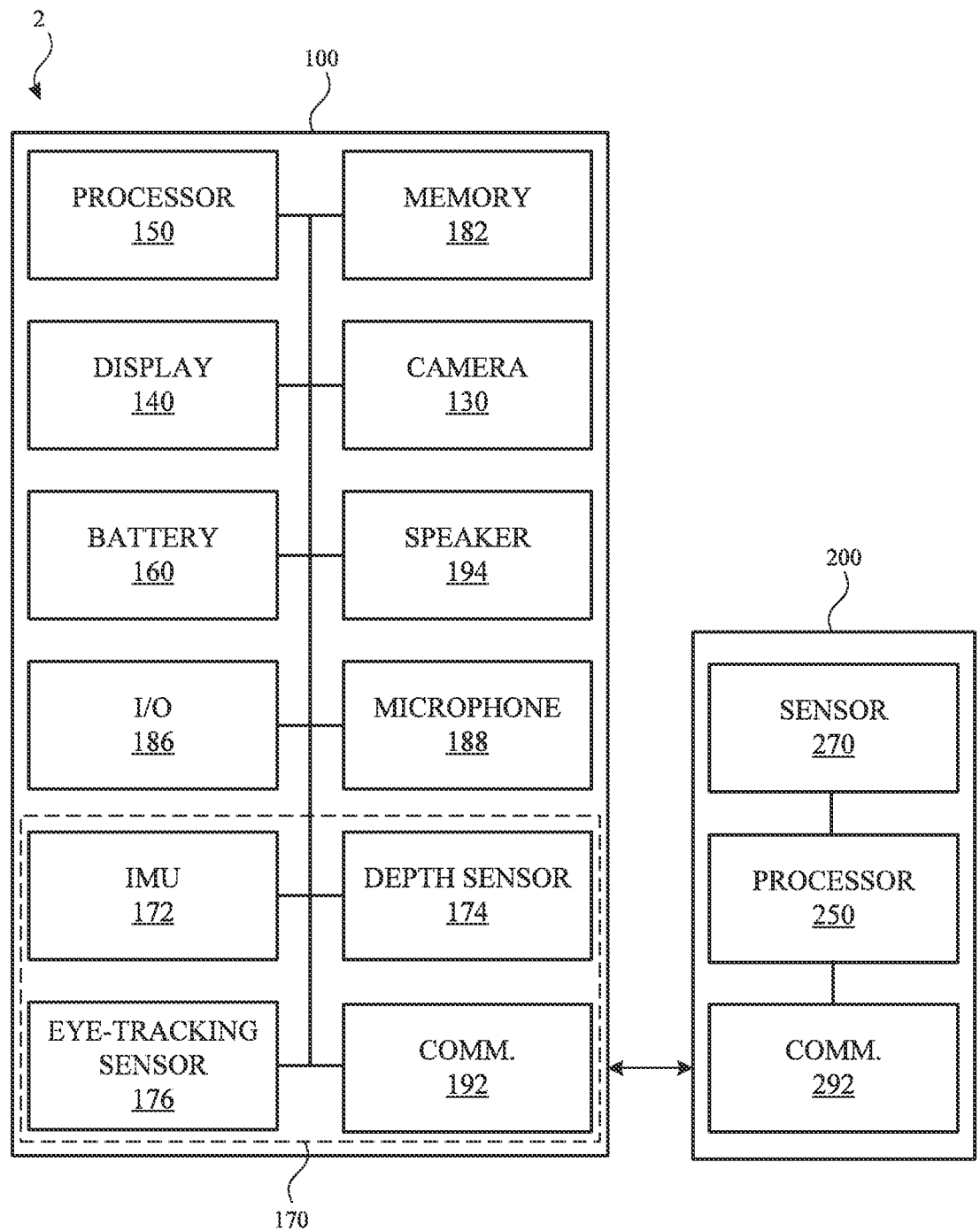
FIG. 9 illustrates a block diagram of a head-mountable device, in accordance with some embodiments of the present disclosure.

Referring now to FIG. 9, components of the head-mountable device can be operably connected to provide the performance described herein. FIG. 9 shows a simplified block diagram of an illustrative head-mountable device 100 in accordance with one embodiment of the invention. It will be appreciated that components described herein can be provided on one, some, or all of a housing, a securement element, and/or a crown module. It will be understood that additional components, different components, or fewer components than those illustrated may be utilized within the scope of the subject disclosure.

As shown in FIG. 9, the head-mountable device 100 can include a processor 150 (e.g., control circuity) with one or more processing units that include or are configured to access a memory 182 having instructions stored thereon. The instructions or computer programs may be configured to perform one or more of the operations or functions described with respect to the head-mountable device 100. The processor 150 can be implemented as any electronic device capable of processing, receiving, or transmitting data or instructions. For example, the processor 150 may include one or more of: a processor, a microprocessor, a central processing unit (CPU), an application-specific integrated circuit (ASIC), a digital signal processor (DSP), or combinations of such devices. As described herein, the term "processor" is meant to encompass a single processor or processing unit, multiple processors, multiple processing units, or other suitably configured computing element or elements.

The memory 182 can store electronic data that can be used by the head-mountable device 100. For example, the memory 182 can store electrical data or content such as, for example, audio and video files, documents and applications, device settings and user preferences, timing and control signals or data for the various modules, data structures or databases, and so on. The memory 182 can be configured as any type of memory. By way of example only, the memory 182 can be implemented as random access memory, read-only memory, Flash memory, removable memory, or other types of storage elements, or combinations of such devices.

The head-mountable device 100 can further include a display 140 for displaying visual information for a user. The display 140 can provide visual (e.g., image or video) output. The display 140 can be or include an opaque, transparent, and/or translucent display. The display 140 may have a transparent or translucent medium through which light representative of images is directed to a user's eyes. The display 140 may utilize digital light projection, OLEDs, LEDs, uLEDs, liquid crystal on silicon, laser scanning light source, or any combination of these technologies. The medium may be an optical waveguide, a hologram medium, an optical combiner, an optical reflector, or any combination thereof. In one embodiment, the transparent or translucent display may be configured to become opaque selectively. Projection-based systems may employ retinal projection technology that projects graphical images onto a person's retina. Projection systems also may be configured to project virtual objects into the physical environment, for example, as a hologram or on a physical surface. The head-mountable device 100 can include an optical subassembly configured to help optically adjust and correctly project the image-based content being displayed by the display 140 for close up viewing. The optical subassembly can include one or more lenses, mirrors, or other optical devices.

The head-mountable device 100 can include a battery 160, which can charge and/or power components of the head-mountable device 100. The battery 160 can also charge and/or power components connected to the head-mountable device 100.

The head-mountable device 100 can include an input/output component 186, which can include any suitable component for connecting head-mountable device 100 to other devices. Suitable components can include, for example, audio/video jacks, data connectors, or any additional or alternative input/output components. The input/output component 186 can include buttons, keys, or another feature that can act as a keyboard for operation by the user.

The head-mountable device 100 can include the microphone 188 as described herein. The microphone 188 can be operably connected to the processor 150 for detection of sound levels and communication of detections for further processing, as described further herein.

The head-mountable device 100 can include the speakers 194 as described herein. The speakers 194 can be operably connected to the processor 150 for control of speaker output, including sound levels, as described further herein.

The head-mountable device 100 can include a posture detection system 170, as described herein. The posture detection system 170 can include one or more sensors and/or communication elements. For example, the posture detection system 170 can include an IMU 172, a depth sensor 174, an eye-tracking sensor 176, and/or a communication element 192.

The eye-tracking sensor 176 can track features of the user wearing the head-mountable device 100, including conditions of the user's eye (e.g., focal distance, pupil size, etc.). For example, an eye sensor can optically capture a view of an eye (e.g., pupil) and determine a direction of a gaze of the user. Such eye tracking may be used to determine a location and/or direction of interest with respect to the display 140 and/or elements presented thereon. User interface elements can then be provided on the display 140 based on this information, for example in a region along the direction of the user's gaze or a region other than the current gaze direction, as described further herein. The detections made by the eye-tracking sensor 176 can determine user actions that are interpreted as user inputs. Such user inputs can be used alone or in combination with other user inputs to perform certain actions. By further example, such sensors can perform facial feature detection, facial movement detection, facial recognition, user mood detection, user emotion detection, voice detection, and the like.

The head-mountable device 100 and/or the posture detection system 170 can include one or more other sensors. Such sensors can be configured to sense substantially any type of characteristic such as, but not limited to, images, pressure, light, touch, force, temperature, position, motion, and so on. For example, the sensor can be a photodetector, a temperature sensor, a light or optical sensor, an atmospheric pressure sensor, a humidity sensor, a magnet, a gyroscope, an accelerometer, a chemical sensor, an ozone sensor, a particulate count sensor, and so on. By further example, the sensor can be a bio-sensor for tracking biometric characteristics, such as health and activity metrics.

The head-mountable device 100 can include a communication element 192 for communicating with one or more servers or other devices using any suitable communications protocol. For example, communication element 192 can support Wi-Fi (e.g., a 802.11 protocol), Ethernet, Bluetooth, high frequency systems (e.g., 1400 MHz, 2.4 GHz, and 5.6 GHz communication systems), infrared, TCP/IP (e.g., any of the protocols used in each of the TCP/IP layers), HTTP, BitTorrent, FTP, RTP, RTSP, SSH, any other communications protocol, or any combination thereof. A communication element 192 can also include an antenna for transmitting and receiving electromagnetic signals.

A system 2 including the head-mountable device 100 can further include an external device 200. The external device 200 can facilitate posture detection and operate in concert with the head-mountable device 100, as described herein.

The external device 200 can include a processor 250 (e.g., control circuitry) with one or more processing units that include or are configured to access a memory having instructions stored thereon. The instructions or computer programs may be configured to perform one or more of the operations or functions described with respect to the external device 200. The processor 250 can be implemented as any electronic device capable of processing, receiving, or transmitting data or instructions. For example, the processor 250 may include one or more of: a processor, a microprocessor, a central processing unit (CPU), an application-specific integrated circuit (ASIC), a digital signal processor (DSP), or combinations of such devices. As described herein, the term "processor" is meant to encompass a single processor or processing unit, multiple processors, multiple processing units, or other suitably configured computing element or elements.

The external device 200 can include one or more sensors 270 of a posture detection system, as described herein. The posture detection system of the external device 200 can include one or more sensors and/or communication elements. The sensors 270 can include sensors for detecting body portions of the user, the head-mountable device 100, and/or another external device 200. For example, the posture detection system can include an IMU, a depth sensor, and the like.

The external device 200 can include a communication element 292 for communicating with one or more servers or other devices using any suitable communications protocol. For example, communication element 292 can support Wi-Fi (e.g., a 802.11 protocol), Ethernet, Bluetooth, high frequency systems (e.g., 1400 MHz, 2.4 GHz, and 5.6 GHz communication systems), infrared, TCP/IP (e.g., any of the protocols used in each of the TCP/IP layers), HTTP, BitTorrent, FTP, RTP, RTSP, SSH, any other communications protocol, or any combination thereof. A communication element 292 can also include an antenna for transmitting and receiving electromagnetic signals.

Accordingly, embodiments of the present disclosure provide a head-mountable device with posture monitoring and feedback. The head-mountable device can detect movement and/or stasis of the user and determine whether motion would be recommended. Upon determining that motion, an additional motion, or a different motion would be beneficial, the head-mountable device can provide an output to the user that promote such motions. The output can include a notification to the user and/or a modification of the user interface that encourages the user to move in a particular way. Such a head-mountable device can provide immersive experiences while the user wearing the head-mountable device benefits from activities that include body motion and promote the user's health.

Various examples of aspects of the disclosure are described below as clauses for convenience. These are provided as examples, and do not limit the subject technology.

Clause A: a head-mountable device comprising: a camera configured to capture an image; a display configured to provide a view based on the image; a detection system configured to detect a stasis of the head-mountable device across a duration of time; and a processor configured to: compare the stasis of the head-mountable device to a threshold; and if the stasis exceeds a threshold, provide an output to a user to prompt motion of the user.

Clause B: a head-mountable device comprising: a posture detection system; and a processor configured to: operate the posture detection system to determine a current posture of the user; compare the current posture to a target posture; and provide an output that prompts a user to move to the target posture.

Clause C: a head-mountable device comprising: a display configured to provide a user interface; a processor configured to: receive an indicator corresponding to a posture of the user; based on the indicator, determine a recommended adjustment of the posture of the user; and modify the user interface to provide a visual element on a side of the user interface that corresponds to a direction of the recommended adjustment of the posture of the user.

One or more of the above clauses can include one or more of the features described below. It is noted that any of the following clauses may be combined in any combination with each other, and placed into a respective independent clause, e.g., clause A, B, or C.

Clause 1: a frame; a camera on an outer side of the frame; a speaker; and a microphone.

Clause 2: the detection system comprises an inertial measurement unit.

Clause 3: the detection system comprises a depth sensor configured to detect a body portion of the user.

Clause 4: the detection system comprises a sensor configured to detect an external device worn on a body portion of the user.

Clause 5: the detection system comprises a sensor configured to detect an external device that is not attached to the user.

Clause 6: the motion of the user comprises changing an angle formed by a head and a torso of the user.

Clause 7: determining the current posture of the user comprises determining a position and orientation of a head with respect to another body portion of the user.

Clause 8: the target posture is a posture that is different than the current posture after the current posture has been maintained for a duration a time that exceeds a threshold.

Clause 9: the posture detection system comprises a communication element operably connected to an external device that detects the current posture of the user.

Clause 10: a display, wherein the output comprises a visual element on the display.

Clause 11: in the current posture, a first angle is formed by a head and a torso of the user; and in the target posture, a second angle, different than the first angle, is formed by the head and the torso.

Clause 12: the visual element of the user interface is repositionable within the user interface based on a change of orientation of the head-mountable device.

Clause 13: the processor is further configured to move the visual element outside a boundary of the user interface if a user does not perform to the recommended adjustment within a time limit.

Clause 14: the recommended adjustment comprises changing an angle formed by a head and a torso of the user.

Clause 15: a posture detection system, wherein the indicator is generated by the posture detection system.

Clause 16: the indicator is received from an external device worn by the user.

Clause 17: the indicator is received from an external device that is not worn by the user.

As described above, one aspect of the present technology may include the gathering and use of data available from various sources. The present disclosure contemplates that in some instances, this gathered data may include personal information data that uniquely identifies or can be used to contact or locate a specific person. Such personal information data can include demographic data, location-based data, telephone numbers, email addresses, twitter ID's, home addresses, data or records relating to a user's health or level of fitness (e.g., vital signs measurements, medication information, exercise information), date of birth, or any other identifying or personal information.

The present disclosure recognizes that the use of such personal information data, in the present technology, can be used to the benefit of users. For instance, health and fitness data may be used to provide insights into a user's general wellness, or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the US, collection of or access to certain health data may be governed by federal and/or state laws, such as the Health Insurance Portability and Accountability Act (HIPAA); whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of advertisement delivery services, the present technology can be configured to allow users to select to "opt in" or "opt out" of participation in the collection of personal information data during registration for services or anytime thereafter. In another example, users can select not to provide mood-associated data for targeted content delivery services. In yet another example, users can select to limit the length of time mood-associated data is maintained or entirely prohibit the development of a baseline mood profile. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data a city level rather than at an address level), controlling how data is stored (e.g., aggregating data across users), and/or other methods.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, content can be selected and delivered to users by inferring preferences based on non-personal information data or a bare minimum amount of personal information, such as the content being requested by the device associated with a user, other non-personal information available to the content delivery services, or publicly available information.

A reference to an element in the singular is not intended to mean one and only one unless specifically so stated, but rather one or more. For example, "a" module may refer to one or more modules. An element proceeded by "a," "an," "the," or "said" does not, without further constraints, preclude the existence of additional same elements.

Headings and subheadings, if any, are used for convenience only and do not limit the invention. The word exemplary is used to mean serving as an example or illustration. To the extent that the term include, have, or the like is used, such term is intended to be inclusive in a manner similar to the term comprise as comprise is interpreted when employed as a transitional word in a claim. Relational terms such as first and second and the like may be used to distinguish one entity or action from another without necessarily requiring or implying any actual such relationship or order between such entities or actions.

Phrases such as an aspect, the aspect, another aspect, some aspects, one or more aspects, an implementation, the implementation, another implementation, some implementations, one or more implementations, an embodiment, the embodiment, another embodiment, some embodiments, one or more embodiments, a configuration, the configuration, another configuration, some configurations, one or more configurations, the subject technology, the disclosure, the present disclosure, other variations thereof and alike are for convenience and do not imply that a disclosure relating to such phrase(s) is essential to the subject technology or that such disclosure applies to all configurations of the subject technology. A disclosure relating to such phrase(s) may apply to all configurations, or one or more configurations. A disclosure relating to such phrase(s) may provide one or more examples. A phrase such as an aspect or some aspects may refer to one or more aspects and vice versa, and this applies similarly to other foregoing phrases.

A phrase "at least one of" preceding a series of items, with the terms "and" or "or" to separate any of the items, modifies the list as a whole, rather than each member of the list. The phrase "at least one of" does not require selection of at least one item; rather, the phrase allows a meaning that includes at least one of any one of the items, and/or at least one of any combination of the items, and/or at least one of each of the items. By way of example, each of the phrases "at least one of A, B, and C" or "at least one of A, B, or C" refers to only A, only B, or only C; any combination of A, B, and C; and/or at least one of each of A, B, and C.

It is understood that the specific order or hierarchy of steps, operations, or processes disclosed is an illustration of exemplary approaches. Unless explicitly stated otherwise, it is understood that the specific order or hierarchy of steps, operations, or processes may be performed in different order. Some of the steps, operations, or processes may be performed simultaneously. The accompanying method claims, if any, present elements of the various steps, operations or processes in a sample order, and are not meant to be limited to the specific order or hierarchy presented. These may be performed in serial, linearly, in parallel or in different order. It should be understood that the described instructions, operations, and systems can generally be integrated together in a single software/hardware product or packaged into multiple software/hardware products.

In one aspect, a term coupled or the like may refer to being directly coupled. In another aspect, a term coupled or the like may refer to being indirectly coupled.

Terms such as top, bottom, front, rear, side, horizontal, vertical, and the like refer to an arbitrary frame of reference, rather than to the ordinary gravitational frame of reference. Thus, such a term may extend upwardly, downwardly, diagonally, or horizontally in a gravitational frame of reference.

The disclosure is provided to enable any person skilled in the art to practice the various aspects described herein. In some instances, well-known structures and components are shown in block diagram form in order to avoid obscuring the concepts of the subject technology. The disclosure provides various examples of the subject technology, and the subject technology is not limited to these examples. Various modifications to these aspects will be readily apparent to those skilled in the art, and the principles described herein may be applied to other aspects.

All structural and functional equivalents to the elements of the various aspects described throughout the disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for".

The title, background, brief description of the drawings, abstract, and drawings are hereby incorporated into the disclosure and are provided as illustrative examples of the disclosure, not as restrictive descriptions. It is submitted with the understanding that they will not be used to limit the scope or meaning of the claims. In addition, in the detailed description, it can be seen that the description provides illustrative examples and the various features are grouped together in various implementations for the purpose of streamlining the disclosure. The method of disclosure is not to be interpreted as reflecting an intention that the claimed subject matter requires more features than are expressly recited in each claim. Rather, as the claims reflect, inventive subject matter lies in less than all features of a single disclosed configuration or operation. The claims are hereby incorporated into the detailed description, with each claim standing on its own as a separately claimed subject matter.

The claims are not intended to be limited to the aspects described herein, but are to be accorded the full scope consistent with the language of the claims and to encompass all legal equivalents. Notwithstanding, none of the claims are intended to embrace subject matter that fails to satisfy the requirements of the applicable patent law, nor should they be interpreted in such a way.

What is claimed is:

1. A head-mountable device comprising:
   a camera configured to capture an image;

a display configured to provide a user interface with a view based on the image;
a detection system configured to detect a stasis of the head-mountable device across a duration of time; and
a processor configured to:
operate the display to provide the view including a visual feature;
compare the stasis of the head-mountable device to a threshold;
when the stasis exceeds the threshold, determine a recommended adjustment of the head-mountable device; and
while the head-mountable device maintains the stasis, provide an output to a user to prompt motion of the user, the output comprising moving the visual feature until the visual feature is outside of the user interface.

2. The head-mountable device of claim 1, further comprising:
a frame;
the camera on an outer side of the frame;
a speaker; and
a microphone.

3. The head-mountable device of claim 1, wherein the detection system comprises an inertial measurement unit.

4. The head-mountable device of claim 1, wherein the detection system comprises a depth sensor configured to detect a body portion of the user.

5. The head-mountable device of claim 1, wherein the detection system comprises a sensor configured to detect an external device worn on a body portion of the user.

6. The head-mountable device of claim 1, wherein the detection system comprises a sensor configured to detect an external device that is not attached to the user.

7. The head-mountable device of claim 1, wherein the motion of the user comprises changing an angle formed by a head and a torso of the user.

8. A head-mountable device comprising:
a posture detection system; and
a display configured to provide a user interface with a view with a visual feature;
a processor configured to:
operate the posture detection system to determine a current posture of a user;
while the user maintains the current posture, operate the display to provide the view with the visual feature;
compare the current posture to a target posture; and
while the user maintains the current posture, provide an output that prompts the user to move to the target posture by moving the visual feature until the visual feature is outside of the user interface.

9. The head-mountable device of claim 8, wherein determining the current posture of the user comprises determining a position and orientation of a head with respect to another body portion of the user.

10. The head-mountable device of claim 8, wherein the target posture is a posture that is different than the current posture after the current posture has been maintained for a duration of time that exceeds a threshold.

11. The head-mountable device of claim 8, wherein the posture detection system comprises a communication element operably connected to an external device that detects the current posture of the user.

12. The head-mountable device of claim 8, wherein:
in the current posture, a first angle is formed by a head and a torso of the user; and
in the target posture, a second angle, different than the first angle, is formed by the head and the torso.

13. A head-mountable device comprising:
a display configured to provide a user interface;
a processor configured to:
receive an indicator corresponding to a posture of a user;
while the user maintains the posture, operate the display to present a visual feature at a first location in the user interface;
based on the indicator, determine a recommended adjustment of the posture of the user; and
while the user maintains the posture, modify the user interface to move the visual feature from the first location to a second location beyond a boundary on a side of the user interface that corresponds to a direction of the recommended adjustment of the posture of the user.

14. The head-mountable device of claim 13, wherein the visual feature of the user interface is repositionable within the user interface based on a change of orientation of the head-mountable device.

15. The head-mountable device of claim 13, wherein the processor is further configured to move the visual feature outside the boundary of the user interface when the user does not perform the recommended adjustment within a time limit.

16. The head-mountable device of claim 13, wherein the recommended adjustment comprises changing an angle formed by a head and a torso of the user.

17. The head-mountable device of claim 13, further comprising a posture detection system, wherein the indicator is generated by the posture detection system.

18. The head-mountable device of claim 13, wherein the indicator is received from an external device worn by the user.

19. The head-mountable device of claim 13, wherein the indicator is received from an external device that is not worn by the user.

* * * * *